United States Patent
Nakabayashi et al.

(10) Patent No.: US 12,040,056 B2
(45) Date of Patent: Jul. 16, 2024

(54) METHOD FOR EVALUATING SYNTHETIC APTITUDE OF COMPOUND, PROGRAM FOR EVALUATING SYNTHETIC APTITUDE OF COMPOUND, AND DEVICE FOR EVALUATING SYNTHETIC APTITUDE OF COMPOUND

(71) Applicant: FUJIFILM Corporation, Tokyo (JP)

(72) Inventors: Jun Nakabayashi, Ashigarakami-gun (JP); Daisuke Terada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 538 days.

(21) Appl. No.: 17/192,484

(22) Filed: Mar. 4, 2021

(65) Prior Publication Data

US 2021/0193272 A1   Jun. 24, 2021

Related U.S. Application Data

(63) Continuation of application No. PCT/JP2019/036072, filed on Sep. 13, 2019.

(30) Foreign Application Priority Data

Sep. 14, 2018   (JP) .................. 2018-172576

(51) Int. Cl.
G16C 20/30   (2019.01)

(52) U.S. Cl.
CPC .................. *G16C 20/30* (2019.02)

(58) Field of Classification Search
CPC .................. G16C 20/30

(Continued)

(56) References Cited

U.S. PATENT DOCUMENTS

| 5,434,796 A | 7/1995 | Weininger |
| 2002/0052694 A1 | 5/2002 | McGregor et al. |

(Continued)

FOREIGN PATENT DOCUMENTS

| JP | 8-512159 A | 12/1996 |
| JP | 2000-29858 A | 1/2000 |

(Continued)

OTHER PUBLICATIONS

U.S. Appl. No. 17/192,530, filed Mar. 4, 2021.

(Continued)

*Primary Examiner* — Ricky Go
(74) *Attorney, Agent, or Firm* — Birch, Stewart, Kolasch & Birch, LLP (57) ABSTRACT

The present invention provides a method for evaluating a synthetic aptitude of a compound, a program for evaluating a synthetic aptitude of a compound, and a device for evaluating a synthetic aptitude of a compound, which evaluate a synthetic aptitude of a compound generated and/or modified on a computer. The present invention relates to a method for evaluating a synthetic aptitude of a compound, the method including a step of selecting a compound database storing a plurality of reference compounds, a step of deciding a structure of a compound to be evaluated for the synthetic aptitude, a step of extracting a reference atomic arrangement from a structure of the reference compound stored in the compound database and obtaining a reference appearance frequency of the reference atomic arrangement, a step of extracting an atomic arrangement from the structure of the compound and obtaining an appearance frequency of the atomic arrangement, and a step of evaluating the synthetic aptitude based on the number of bonds included in the atomic arrangement of the compound and the appearance frequency of the reference atomic arrangement (Continued)

corresponding to the atomic arrangement; a program to execute the method; and a device to execute the method.

9 Claims, 9 Drawing Sheets

(58) Field of Classification Search
USPC .......................................................... 702/27
See application file for complete search history.

(56) References Cited

U.S. PATENT DOCUMENTS

| | | | |
|---|---|---|---|
| 2004/0083060 A1* | 4/2004 | Church | G16C 20/40 |
| | | | 702/19 |
| 2008/0027652 A1 | 1/2008 | Cramer et al. | |
| 2010/0145896 A1 | 6/2010 | Yuta | |
| 2010/0312538 A1* | 12/2010 | Umeyama | G16C 20/64 |
| | | | 703/12 |
| 2011/0029296 A1* | 2/2011 | Ciloy | G16B 15/30 |
| | | | 703/11 |
| 2012/0330632 A1 | 12/2012 | Oganov et al. | |
| 2013/0226549 A1* | 8/2013 | Tseng | G16B 15/30 |
| | | | 703/11 |
| 2015/0310162 A1 | 10/2015 | Okuno et al. | |
| 2017/0124482 A1 | 5/2017 | Yoo et al. | |
| 2018/0052979 A1 | 2/2018 | Bito et al. | |

FOREIGN PATENT DOCUMENTS

| | | |
|---|---|---|
| JP | 2002-514811 A | 5/2002 |
| JP | 2002-530727 A | 9/2002 |
| JP | 2003-206246 A | 7/2003 |
| JP | 5083320 B2 | 11/2012 |
| JP | 2017-91526 A | 5/2017 |
| JP | 2018-32077 A | 3/2018 |
| WO | WO 99/59061 A1 | 11/1999 |
| WO | WO 00/39751 A2 | 7/2000 |
| WO | WO 2009/064015 A1 | 5/2009 |
| WO | WO 2014/034577 A1 | 3/2014 |

OTHER PUBLICATIONS

U.S. Appl. No. 17/192,034, filed Mar. 4, 2021.
Ertl et al., "Estimation of synthetic accessibility score of drug-like molecules based on molecular complexity and fragment contributions," Journal of Cheminformatics, vol. 1, No. 8, Jun. 10, 2009, pp. 1-11.
Ikebata et al., "Bayesian molecular design with a chemical language model," J. Comput. Aided. Mol. Des., vol. 31, 2017 (published online Mar. 9, 2017), pp. 379-391.
International Preliminary Report on Patentability and Written Opinion of the International Searching Authority (Forms PCT/IB/326, PCT/IB/373, and PCT/ISA/237) for International Application No. PCT/JP2019/036072, dated Mar. 25, 2021, with English translation of the Written Opinion.
International Search Report (Form PCT/ISA/210) for International Application No. PCT/JP2019/036072, dated Dec. 3, 2019, with English translation.
Tanimura, "De novo drug design that approached the stage of maturation," CICSJ Bulletin, vol. 28, No. 3, 2010, pp. 57-61.
International Preliminary Report on Patentability and Written Opinion of the International Searching Authority (Forms PCT/IB/326, PCT/IB/373 and PCT/ISA/237) for International Application No. PCT/JP2019/036074, dated Mar. 25, 2021, with English translation of the Written Opinion.
International Preliminary Report on Patentability and Written Opinion of the International Searching Authority (Forms PCT/IB/326, PCT/IB/373, and PCT/ISA/237) for International Application No. PCT/JP2019/036073, dated Mar. 25, 2021, with English translation of the Written Opinion.
International Search Report (Form PCT/ISA/210) for International Application No. PCT/JP2019/036074, dated Dec. 17, 2019, with English translation.
International Search Report (PCT/ISA/210) for International Application No. PCT/JP2019/036073, dated Dec. 10, 2019, with English translation.
Kawai et al., "Molecular Evolutionary Algorithm for Structure Design and Structure Generation," J. Comput. Chem. Jpn., vol. 10, No. 1, 2011, pp. 25-31 (7 pages total), with English abstract.
Kyoto Constella Technologies Co., Ltd., "ReCGen (Refined Compound Generator)," URL:http://recgen.czeek.jp/recgen/, retrieved Jul. 23, 2018, 4 pages total.
Matsuyama et al., "Development of a molecular fingerprint ensemble method for discovery of active compounds with diverse structures," IPSJ Technical Report: Bioinformatics, vol. 2018-BIO-53, No. 9, Mar. 2, 2018, pp. 1-6 (8 pages total), with English abstract.
Indian Office Action for Indian Application No. 202147010005, dated Jun. 27, 2023, with English translation.
Indian Office Action for Indian Application No. 202147010004, dated Nov. 17, 2022, with an English translation.
Japanese Notice of Reasons for Refusal for Japanese Application No. 2020-546219, dated Apr. 26, 2022, with an English translation.
Boda et al., "Structure and reaction based evaluation of synthetic accessibility," J Comput Aided Mol Des, vol. 21, 2007 (Published online Feb. 9, 2007), pp. 311-325.
Extended European Search Report for European Application No. 19858853.5, dated Sep. 17, 2021.
Extended European Search Report for European Application No. 19859449.1, dated Sep. 24. 2021.
Extended European Search Report for European Application No. 19860042.1, dated Oct. 7, 2021.
Globus et al., "Automatic molecular design using evolutionary techniques," Nanotechnology, vol. 10, 1999, pp. 290-299, XP-000878962.
Olivecrona et al., "Molecular de-nevo design through deep reinforcement learning," Journal of Cheminformatics, vol. 9, No. 48, 2017, pp. 1-14.
Indian Office Action for Indian Application No. 202147009975, dated Jan. 6, 2023, with an English translation.
Japanese Notice of Reasons for Refusal for Japanese Application No. 2020-546217, dated Jun. 10, 2022, with an English translation.
Japanese Notice of Reasons for Refusal for Japanese Application No. 2020-546218, dated Jun. 6, 2022, with an English translation.
Indian Office Action for Indian Application No. 202147010004, dated Dec. 26, 2023, with English translation.
Indian Office Action for Indian Application No. 202147010005, dated Mar. 14, 2024, with an English translation.
Fonseca et al., "Multiobjective Optimization and Multiple Constraint Handling with Evolutionary Algorithms—Part I: A Unified Formulation," IEEE Transactions on Systems, Man, and Cybernetics—Part A: Systems and Humans, vol. 28, No. 1, 1998, pp. 26-37.
Nicolaou, "Graph Design Using Knowledge-Driven, Self-Adaptive Multi-Objective Evolutionary Graph Algorithms," University of Cyprus [Dissertation], 2010, 199 pages total.
Turner et al., "Rapid Quantification of Molecular Diversity for Selective Database Acquisition," Journal of Chemical Information & Computer Sciences, vol. 37, 1997, pp. 18-22.
U.S. Office Action for U.S. Appl. No. 17/192,034, dated Jun. 3, 2024.

* cited by examiner

ONE BOND

| ATOMIC ARRANGEMENT | APPEARANCE FREQUENCY |
|---|---|
| C.ar : C.ar | 799082034 |
| C.3 – C.3 | 427869724 |
| ... | ... |
| I#S.3 | 1 |

FIVE BONDS

| ATOMIC ARRANGEMENT | APPEARANCE FREQUENCY |
|---|---|
| C.ar : C.ar : C.ar : C.ar : C.ar | 765522244 |
| C.3–C.3–C.3–C.3–C.3 | 180664124 |
| ... | ... |
| C.ar – C.ar : C.ar = C.2 – N.pl3 – O.co2 | 1 |

(– IS A SINGLE BOND, = IS A DOUBLE BOND, # IS A TRIPLE BOND, AND : IS aromatic)

FIG.7

ONE BOND

| ATOMIC ARRANGEMENT | APPEARANCE FREQUENCY |
|---|---|
| C.ar : C.ar | 6 |
| O.3 – C.ar | 1 |
| Br – O.3 | 1 |
| Br – (edge) | 1 |

TWO BONDS

| ATOMIC ARRANGEMENT | APPEARANCE FREQUENCY |
|---|---|
| C.ar : C.ar : C.ar | 6 |
| O.3 – C.ar : C.ar | 2 |
| Br – O.3 – C.ar | 1 |
| O.3 – Br – (edge) | 1 |

THREE BONDS

| ATOMIC ARRANGEMENT | APPEARANCE FREQUENCY |
|---|---|
| C.ar : C.ar : C.ar : C.ar | 6 |
| O.3 – C.ar : C.ar : C.ar | 2 |
| Br – O.3 – C.ar : C.ar | 2 |
| C.ar – O.3 – Br – (edge) | 1 |

FOUR BONDS

| ATOMIC ARRANGEMENT | APPEARANCE FREQUENCY |
|---|---|
| C.ar : C.ar : C.ar : C.ar : C.ar | 6 |
| O.3 – C.ar : C.ar : C.ar : C.ar | 2 |
| Br – O.3 – C.ar : C.ar : C.ar | 2 |
| C.ar : C.ar – O.3 – Br – (edge) | 2 |

FIVE BONDS

| ATOMIC ARRANGEMENT | APPEARANCE FREQUENCY |
|---|---|
| C.ar : C.ar : C.ar : C.ar : C.ar : C.ar | 6 |
| O.3 – C.ar : C.ar : C.ar : C.ar : C.ar | 2 |
| Br – O.3 – C.ar : C.ar : C.ar : C.ar | 2 |
| C.ar : C.ar : C.ar – O.3 – Br – (edge) | 2 |

(edge REPRESENTS A TERMINAL OF MOLECULE)

METHOD FOR EVALUATING SYNTHETIC APTITUDE OF COMPOUND, PROGRAM FOR EVALUATING SYNTHETIC APTITUDE OF COMPOUND, AND DEVICE FOR EVALUATING SYNTHETIC APTITUDE OF COMPOUND

CROSS-REFERENCE TO RELATED APPLICATIONS

The present application is a Continuation of PCT International Application No. PCT/JP2019/036072 filed on Sep. 13, 2019 claiming priority under 35 U.S.C. § 119(a) to Japanese Patent Application No. 2018-172576 filed on Sep. 14, 2018. Each of the above applications is hereby expressly incorporated by reference, in its entirety, into the present application.

BACKGROUND OF THE INVENTION

1. Field of the Invention

The present invention relates to a method for evaluating a synthetic aptitude of a compound, a program for evaluating a synthetic aptitude of a compound, and a device for evaluating a synthetic aptitude of a compound, and particularly relates to a method for evaluating a synthetic aptitude of a compound, a program for evaluating a synthetic aptitude of a compound, and a device for evaluating a synthetic aptitude of a compound, the compound being generated or modified on a computer.

2. Description of the Related Art

In the related art, the search for a structure of a compound having a desired physical property value has been performed mainly by giving a molecular structure and obtaining a physical property value as a result, but with the development of informatics in recent years, studies of giving a physical property value and obtaining a molecular structure having the physical property value are rapidly progressing. For example, "Bayesian molecular design with a chemical language model", Hisaki Ikebata et al., "searched on Jul. 23, 2018", internet (ncbi.nlm.nih.gov/pubmed/28281211) is known as a method for searching a molecular structure from the physical property value. The "Bayesian molecular design with a chemical language model", Hisaki Ikebata et al., "searched on Jul. 23, 2018", internet (ncbi.nlm.nih.gov/pubmed/28281211) discloses that a structure having a physical property value close to the target value is obtained by, giving a target value of physical property value, (1) generating a plurality of initial structures (chemical structures), (2) randomly changing each structure, (3) estimating the physical property value of each structure, and (4) adopting or rejecting the change in structure based on the distance between the physical property value and the target value. In this process, the processes (2) to (4) are repeated. As described above, in order to search the molecular structure from the physical property value, a technique for performing (1) to (4) is required.

In a case of performing the above-described (1) to (4), since it is meaningless in a case where all of the chemical structures obtained in (4) are difficult to synthesize, a technique capable of evaluating a synthetic aptitude of the compound is required. As such an evaluation method, a technique for calculating a synthetic accessibility score (SAscore) has been known (refer to "Estimation of synthetic Accessibility score of drug-like molecules based on molecular complexity and fragment contributions", Peter Ertl and Ansgar Schuffenhauer, Journal of Cheminformatics 2009, 1;8, "searched on Jul. 23, 2018", internet (jcheminf.springeropen.com/articles/10.1186/1758-2946-1-8)).
SAscore has an actual value from 1 to 10, and as the value is smaller, it is considered to be synthesized more easily.

SUMMARY OF THE INVENTION

In SAscore disclosed in the "Estimation of synthetic Accessibility score of drug-like molecules based on molecular complexity and fragment contributions", Peter Ertl and Ansgar Schuffenhauer, Journal of Cheminformatics 2009, 1;8, "searched on Jul. 23, 2018", internet (jcheminf.springeropen.com/articles/10.1186/1758-2946-1-8), an atomic arrangement in a compound is extracted, the atomic arrangement is fragmented with a definition based on ECFC_4 #fragments, the logarithm of an appearance frequency of each fragment in a database is used as a contribution of the fragment, and the contributions of each fragment are summed, thereby obtaining a score. However, in the "Estimation of synthetic Accessibility score of drug-like molecules based on molecular complexity and fragment contributions", Peter Ertl and Ansgar Schuffenhauer, Journal of Cheminformatics 2009, 1;8, "searched on Jul. 23, 2018", internet (jcheminf.springeropen.com/articles/10.1186/1758-2946-1-8), since relatively large fragments or fragments having a complicated branching structure are considered, half of the extracted fragments are fragments appearing only once in the database. The "appearing only once in the database" means that a specific molecule is an individual fragment, and this result suggests that such a molecule-individual fragment is likely to occur based on the ECFC_4 #fragments.

As the extracted fragment is larger, or as the branching structure included in the fragment is more complex, the appearance frequency in the database is smaller. In other words, as the number of bonds included in the fragment is larger, the appearance frequency in the database is smaller. However, such a molecular arrangement may not always be difficult to synthesize, and in some cases, the evaluation of the score with the synthetic aptitude are not performed properly.

As described above, in the evaluation of synthetic aptitude using the compound database in the related art, the synthetic aptitude of the compound cannot be sufficiently evaluated.

The present invention has been studied in view of such circumstances, and an object of the present invention is to provide a method for evaluating a synthetic aptitude of a compound, a program for evaluating a synthetic aptitude of a compound, and a device for evaluating a synthetic aptitude of a compound, which evaluate a synthetic aptitude of a compound generated and/or modified on a computer in order to efficiently search for a structure of the compound.

In order to achieve the object of the present invention, a method for evaluating a synthetic aptitude of a compound according to an aspect of the present invention includes:
- a step of selecting a compound database storing a plurality of reference compounds which serve as evaluation criteria for a synthetic aptitude;
- a step of deciding a structure of a compound to be evaluated for the synthetic aptitude;
- a step of extracting a reference atomic arrangement from a structure of the reference compound stored in the compound database and obtaining a reference appearance frequency of the reference atomic arrangement;

a step of extracting an atomic arrangement from the structure of the compound and obtaining an appearance frequency of the atomic arrangement; and a step of evaluating the synthetic aptitude based on the number of bonds included in the atomic arrangement of the compound and the appearance frequency of the reference atomic arrangement corresponding to the atomic arrangement.

In order to achieve the object of the present invention, a program for evaluating a synthetic aptitude of a compound according to an aspect of the present invention causes a computer to execute the above-described method for evaluating a synthetic aptitude of a compound.

In order to achieve the object of the present invention, a device for evaluating a synthetic aptitude of a compound according to an aspect of the present invention includes:

a database selection part of selecting a compound database storing a plurality of reference compounds which serve as evaluation criteria for a synthetic aptitude;

a structure acquisition part of acquiring a structure of a compound to be evaluated for the synthetic aptitude;

a first extraction part of extracting a reference atomic arrangement from a structure of the reference compound stored in the compound database and obtaining a reference appearance frequency of the reference atomic arrangement;

a second extraction part of extracting an atomic arrangement from the structure of the compound and obtaining an appearance frequency of the atomic arrangement;

a calculation part of calculating, as a partial score, a frequency with which the atomic arrangement appears in the reference compound, and calculating a total score by totaling the partial scores, based on the number of bonds included in the atomic arrangement of the compound and the appearance frequency of the reference atomic arrangement corresponding to the atomic arrangement, using a function in which a numerical value decreases as the number of bonds included in the atomic arrangement and the appearance frequency increase; and an evaluation part of evaluating the synthetic aptitude based on the total score.

With the method for evaluating a synthetic aptitude of a compound according to the aspect of the present invention, the appearance frequency of the atomic arrangement in the compound database, the atomic arrangement being extracted from a compound to be evaluated, is obtained, and the synthetic aptitude is evaluated based μm the number of bonds included in the atomic arrangement and the appearance frequency. By evaluating the synthetic aptitude in consideration of the number of bonds included in the atomic arrangement, the appearance frequency decreases as the number of bonds increases, and the synthetic aptitude of a compound evaluated as having low synthetic aptitude can be evaluated properly.

DESCRIPTION OF THE PREFERRED EMBODIMENTS

Hereinafter, a method for evaluating a synthetic aptitude of a compound, program for evaluating a synthetic aptitude of a compound, and device for evaluating a synthetic aptitude of a compound according to embodiments of the present invention will be described with reference to the accompanying drawings.

<<Device for Evaluating Synthetic Aptitude of Compound>>

Figure 1:
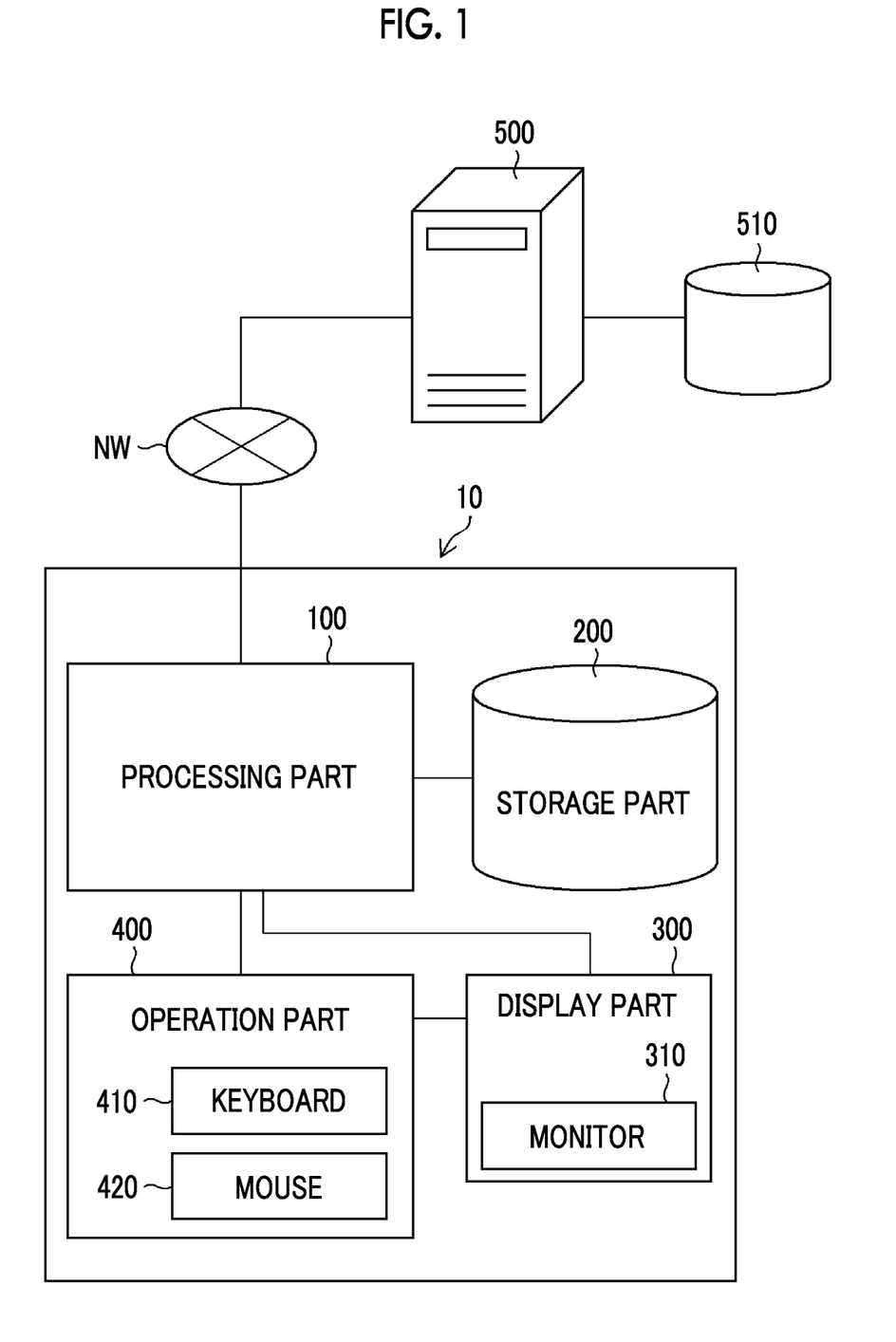
FIG. 1 is a block diagram showing a configuration of a device for evaluating a synthetic aptitude of a compound.

FIG. 1 is a block diagram showing a configuration of a device 10 for evaluating a synthetic aptitude of a compound (hereinafter, also simply referred to as a "synthetic aptitude evaluation device"). The synthetic aptitude evaluation device 10 is a device for evaluating a synthetic aptitude of a compound, and can be realized using a computer. As shown in FIG. 1, the synthetic aptitude evaluation device 10 includes a processing part 100, a storage part 200, a display part 300, and an operation part 400, which are connected to each other to transmit and receive necessary information. Various installation forms can be adopted for these constituents, and each constituent may be installed in one place (one housing, one room, and the like), or may be installed at a distant place and connected through a network. In addition, the synthetic aptitude evaluation device 10 is connected to an external server 500 and an external database 510 through the network NW such as the internet, and can acquire information such as a structural formula of a compound for which the synthetic aptitude is evaluated, and/or structural formulae of a plurality of reference compounds stored in a compound database, as necessary.

<Configuration of Processing Part>

Figure 2:
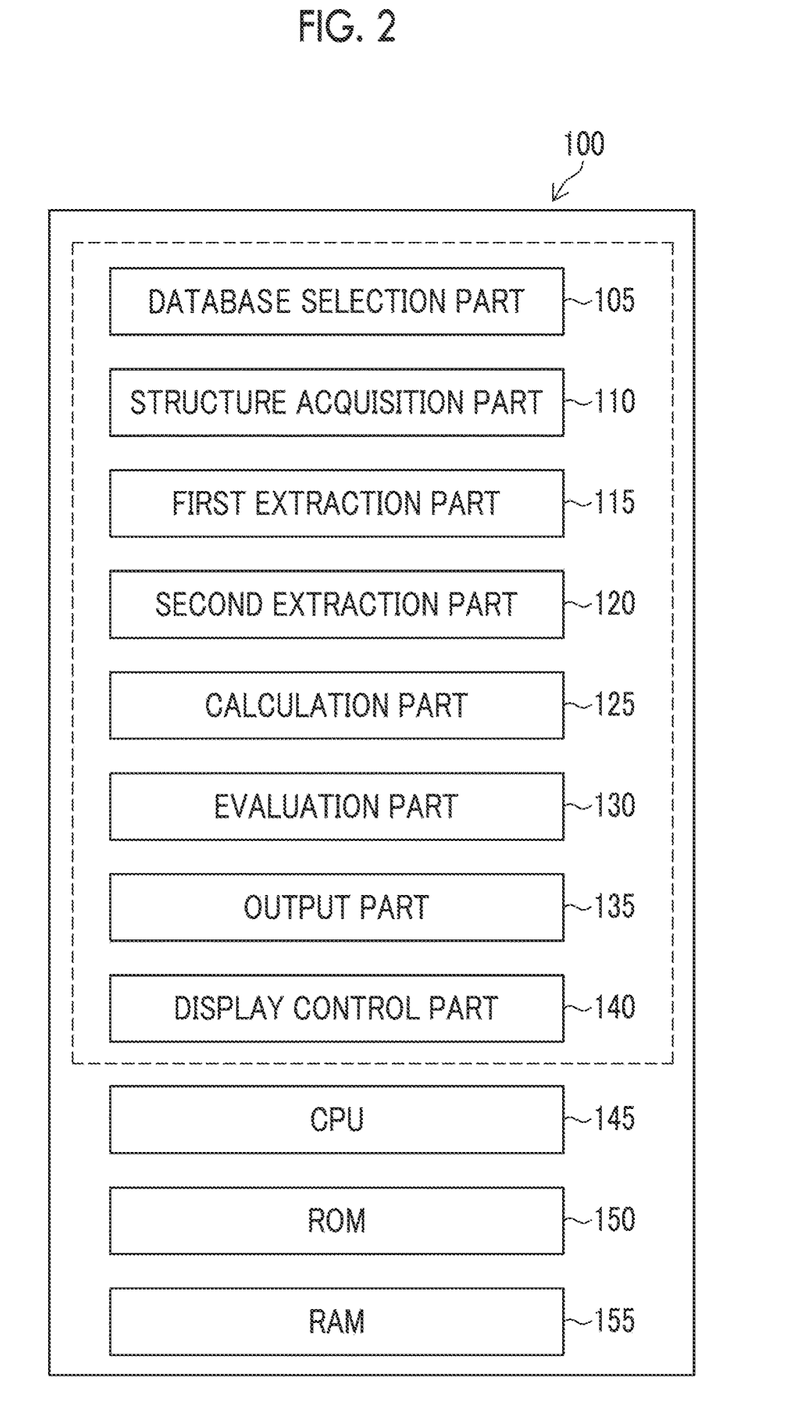
FIG. 2 is a diagram showing a configuration of a processing part.

FIG. 2 is a diagram showing a configuration of the processing part 100. The processing part 100 includes a database selection part 105, a structure acquisition part 110, a first extraction part 115, a second extraction part 120, a calculation part 125, an evaluation part 130, an output part 135, a display control part 140, a central processing unit (CPU) 145, a read only memory (ROM) 150, and a random access memory (RAM) 155.

The database selection part 105 selects, from a plurality of compound databases storing a plurality of reference compounds, a compound database storing a compound suitable for the purpose of evaluating a synthetic aptitude. The compound database can be selected from a plurality of compound databases acquired through a recording medium interface such as a DVD drive and a terminal for semiconductor memory (not shown), and/or a network. The compound database to be selected is preferably a compound database having a high structural diversity, and in a case of a special purpose, a compound database having a structural bias according to the purpose can also be selected. For example, in a case where it is required to determine whether or not a compound to be evaluated for a synthetic aptitude is a coloring agent-based compound, a compound database including many compounds which are coloring agents is selected. In addition, in a case where it is required to determine whether or not a compound to be evaluated for a synthetic aptitude is a medicament-based compound, a compound database including many compounds which are medicaments is selected.

The structure acquisition part 110 acquires information such as a structural formula of the compound through the recording medium interface such as a DVD drive and a terminal for semiconductor memory (not shown), and/or the network. For information such as a structural formula of the compound, a compound generated and/or modified on a computer can be used. In addition, the structural formula of the compound may be input using a keyboard 410 and mouse 420 of the operation part 400.

The first extraction part 115 extracts a reference atomic arrangement from a structure of the reference compound stored in the compound database, and obtains a reference appearance frequency of the reference atomic arrangement.

The second extraction part 120 extracts an atomic arrangement from the structure of the compound for which the synthetic aptitude is evaluated, and obtains an appearance frequency of an atomic arrangement from the compound for which the synthetic aptitude is evaluated.

The calculation part 125 calculates, as a partial score, a frequency with which the atomic arrangement appears in the reference compound, based on the number of bonds included in the atomic arrangement of the compound for which the synthetic aptitude is evaluated, and the reference appearance frequency of the reference atomic arrangement of the compound stored in the compound database. In addition, the calculation part 125 totals the partial scores and calculates the total score.

The evaluation part 130 evaluates the synthetic aptitude based on the total score calculated by the calculation part 125. Since the partial score is obtained using a function in which the numerical value decreases as the number of bonds included in the atomic arrangement and the appearance frequency in the compound database increase, it can be evaluated that the synthetic aptitude is higher as the partial score is smaller, that is, the total score is smaller. In addition, in the compound database selected by the database selection part, in a case where a compound database having a structural bias according to the purpose is selected, the similarity between the compound and the reference compound in the compound database can also be evaluated. For example, in a case where a compound database including many compounds which are coloring agents is selected as the compound database, and the total score calculated is small, it can be identified that the appearance frequency of the atomic arrangement is large in the compounds including many compounds which are coloring agents, and it can be evaluated that the similarity is high. As a result, it can be evaluated that the compound to be evaluated has a high possibility of having properties of a coloring agent.

The output part 135 outputs the structure of the compound to be evaluated for the synthetic aptitude, which is acquired by the structure acquisition part 110. In addition, the output part 135 outputs the reference atomic arrangement and appearance frequency of the reference atomic arrangement extracted by the first extraction part 115, and the atomic arrangement of the compound extracted by the second extraction part 120 and the appearance frequency of the atomic arrangement of the compound. Furthermore, the output part 135 outputs the partial score and total score calculated by the calculation part 125.

The display control part 140 controls display of the acquired information and processing result on a monitor 310. The method for evaluating a synthetic aptitude of a compound using these functions of the processing part 100 will be described in detail later. The process by these functions is performed under the control of CPU 145.

The function of each part of the processing part 100 described above can be realized by using various processors. Examples of the various processors include a CPU that is a general-purpose processor which executes software (program) to realize various functions. In addition, examples of the various processors also include a programmable logic device (PLD) which is a processor in which circuit configuration can be changed after manufacturing, such as a field programmable gate array (FPGA). Furthermore, examples of the various processors also include a dedicated electric circuit which is a processor having a circuit configuration specifically designed to execute a specific process, such as an application specific integrated circuit (ASIC).

The functions of each part may be realized by one processor, or may be realized by combining a plurality of processors. In addition, a plurality of functions may be realized by one processor. As an example of configuring a plurality of functions with one processor, firstly, an aspect that, as typified by a computer such as a client and a server, one processor is configured by a combination of one or more CPUs and software, and this processor realizes the plurality of functions is exemplified. Secondly, an aspect that, as typified by a system on chip (SoC), uses a processor which realizes the functions of the entire system with a single integrated circuit (IC) chip is exemplified. As described above, various functions are composed by using one or more of the above-described various processors as a hardware structure. Furthermore, the hardware structure of these various processors is more specifically an electric circuit (circuitry) in which circuit elements such as semiconductor elements are combined.

In a case where the above-described processor or electric circuit executes a software (program), a processor (computer)-readable code of the software to be executed is stored in a non-temporary recording medium such as ROM 150 (refer to FIG. 2), and the processor refers to the software. The software stored in the non-temporary recording medium includes the program for executing the method for evaluating a synthetic aptitude of a compound according to the embodiment of the present invention. The code may be recorded in a non-temporary recording medium such as various magneto-optical recording devices and semiconductor memories instead of ROM 150. In a case of processing using a software, for example, RAM 155 is used as a temporary storage area, and for example, data stored in an electronically erasable and programmable read only memory (EEPROM) (not shown) can be referred to.

<Configuration of Storage Part>

Figure 3:
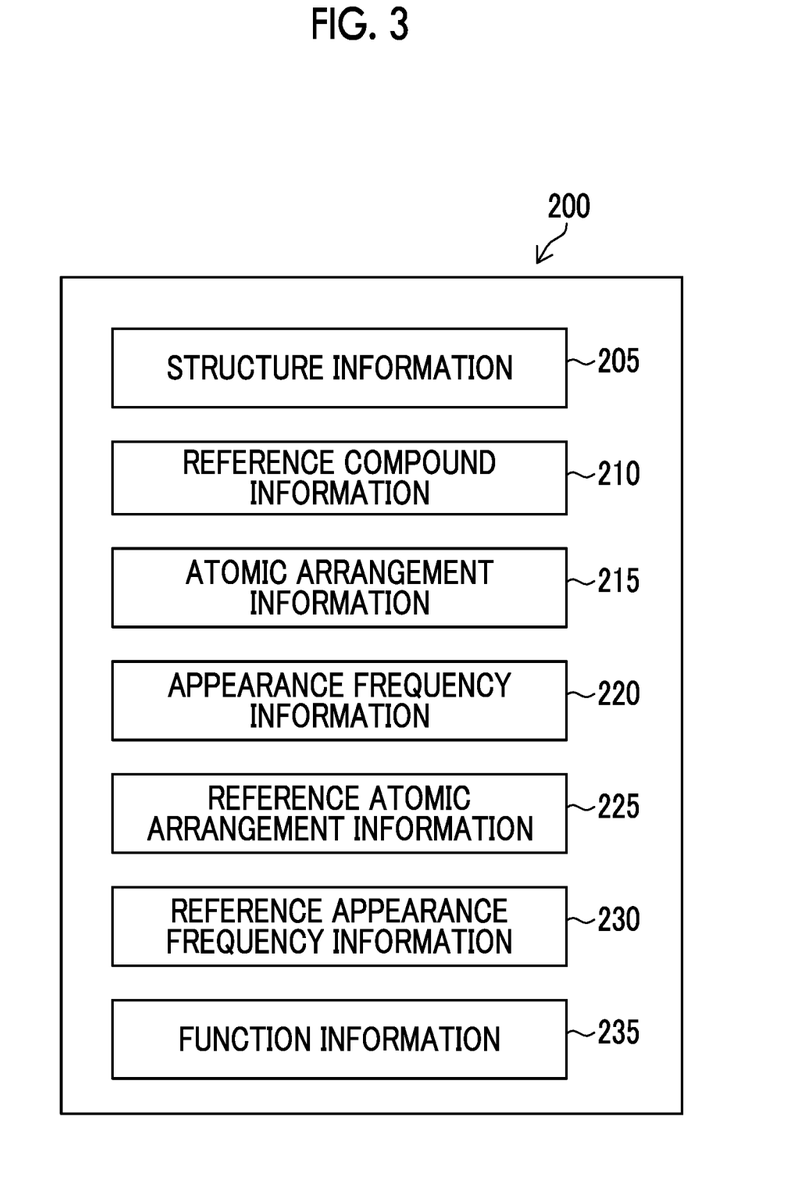
FIG. 3 is a diagram showing information stored in a storage part.

The storage part 200 is configured of a non-temporary recording medium such as a digital versatile disk (DVD), a hard disk, and various semiconductor memories, and a control part thereof, and stores images and information shown in FIG. 3. Structure information 205 includes the structure of the compound to be evaluated for the synthetic aptitude. Reference compound information 210 includes structural formulae of a plurality of reference compounds stored in the compound database. Atomic arrangement information 215 includes atomic arrangements extracted from the compound to be evaluated for the synthetic aptitude. Appearance frequency Information 220 includes frequencies of appearance of the extracted atomic arrangements in the compound to be evaluated for the synthetic aptitude. Reference atomic arrangement information 225 includes reference atomic arrangements extracted from the plurality of reference compounds included in the compound database. Reference appearance frequency information 230 includes appearance reference frequencies of the extracted atomic arrangements in the plurality of reference compounds included in the compound database. Function information 235 includes a function for calculating the partial score and a function for calculating the total score.

<Configuration of Display Part and Operation Part>

The display part 300 includes the monitor 310 (display device), and can display the input image and information, the image and information stored in the storage part 200, the result of process by the processing part 100, and the like. The operation part 400 includes the keyboard 410 and the mouse 420 as input devices and/or pointing devices, and the user can perform operations necessary for executing the method for evaluating a synthetic aptitude of a compound according to the embodiment through these devices and a screen of the monitor 310. Operations which can be performed by the user include input the structure of the compound for which the synthetic aptitude is evaluated, selection of the compound database, specification of an atomic arrangement to be extracted, and the like.

<Process in Device for Evaluating Synthetic Aptitude of Compound>

In the above-described device 10 for evaluating a synthetic aptitude of a compound, a synthetic aptitude of a compound can be evaluated according to the user's instruction through the operation part 400.

<<Method for Evaluating Synthetic Aptitude of Compound>>

Figure 4:
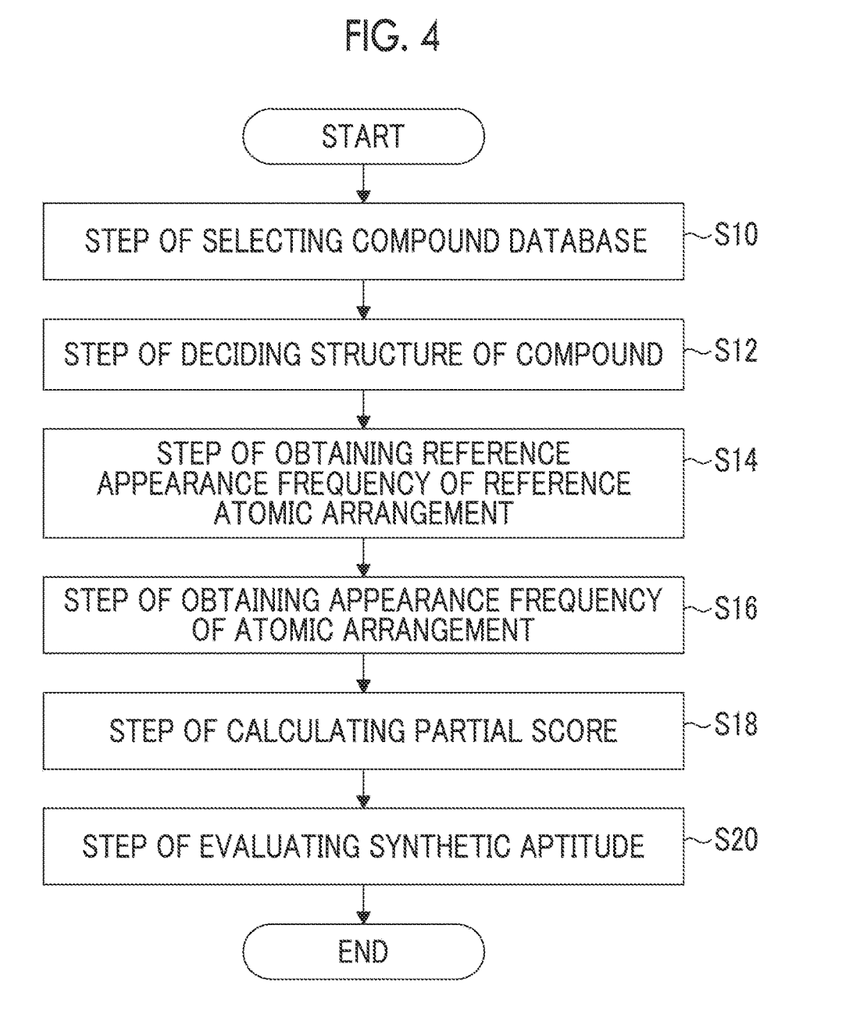
FIG. 4 is a flowchart showing a method for evaluating a synthetic aptitude of a compound.

FIG. 4 is a flowchart showing the method for evaluating a synthetic aptitude of a compound. The method for evaluating a synthetic aptitude includes: a step (Step S10) of selecting a compound database storing a plurality of reference compounds which serve as evaluation criteria for a synthetic aptitude; a step (Step S12) of deciding a structure of a compound for which the synthetic aptitude is evaluated; a step (Step S14) of extracting a reference atomic arrangement from the reference compound stored in the compound database and obtaining a reference appearance frequency of the reference atomic arrangement; a step (Step S16) of extracting an atomic arrangement from the structure of the compound and obtaining an appearance frequency of the atomic arrangement; a step (Step S18) of calculating, as a partial score, a frequency with which the atomic arrangement of the compound appears in the reference compound in the compound database; and a step (Step S20) of evaluating the synthetic aptitude from a total score obtained by totaling the partial scores.

Hereinafter, each step will be described.

<Step of Selecting Compound Database (Step S10)>

The step of selecting a compound database is a step of selecting, from a plurality of compound databases, a compound database which serves as evaluation criteria for a synthetic aptitude. Basically, as the compound database to be selected, a compound database having a high structural diversity is desirable. By selecting a compound database having a high structural diversity, it is possible to evaluate a synthetic aptitude based on various compounds. In addition, in a case where the compound to be evaluated has a special purpose, a compound database having a structural bias according to the purpose may be used. For example, in a case where it is required to determine whether or not the compound is a coloring agent-based compound, a compound database including many known coloring agent compounds can also be selected. In addition, in a case where it is required to determine whether or not the compound is a medicament compound, a compound database including many known medicament compounds can also be selected. As described above, by using a compound database having a structural bias according to a special purpose, it is possible to evaluate whether or not an atomic arrangement appears in the coloring agent compound or medicament compound in the compound database with a high appearance frequency. The case where the appearance frequency is high is considered that the compound to be evaluated has a structure of the reference compound in the selected compound database or a structure close to the atomic arrangement, and is considered that the compound to be evaluated has the same properties as a target compound.

The selection of the compound database may be performed according to the operation of the user, or may be configured to select the compound database by the computer according to conditions desired by the user. As an example of the compound database, PubChem can be used. As the reference compound, all the compounds in the compound database may be used for evaluation, or a part, for example, one million compounds, may be extracted and used for evaluation. As a method for extracting the reference compound from the compound database, compounds may be arbitrarily extracted, or compounds according to a purpose may be extracted so that a database according to the purpose is selected. In the present embodiment, PubChem is used as the compound database, and all the compounds in PubChem are used as the reference compound.

<Step of Deciding Structure of Compound (Step S12)>

Figure 5:
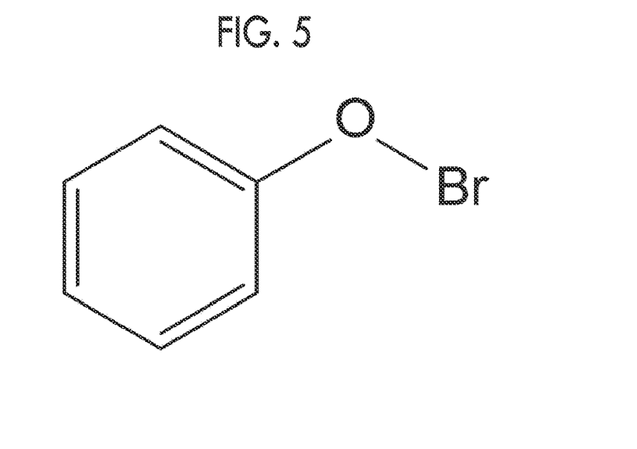
FIG. 5 is a structural formula of a compound for which the synthetic aptitude is evaluated in the present embodiment.

The step of deciding a structure of the compound is a step of deciding a structure of a compound to be evaluated for the synthetic aptitude. In the compound, a structure of the compound may be input according to the operation of the user through the operation part 400 to decide the structure of the compound. In addition, using a structure of a compound in which a structure has been modified in a computer so that desired physical properties can be obtained, the modified compound can also be decided as the compound to be evaluated for the synthetic aptitude. The structure of the compound may be acquired from the external server 500 and the external database 510 through the network NW to be decided. In the present embodiment, as the compound to be evaluated for the synthetic aptitude, a structure of a compound shown in FIG. 5 is exemplified.

<Step of Extracting Reference Atomic Arrangement and Obtaining Reference Appearance Frequency (Step S14)>

The step of extracting a reference atomic arrangement and obtaining a reference appearance frequency is a step of extracting a reference atomic arrangement from the reference compound in the compound database selected in the step S10 and obtaining a reference appearance frequency, which is an appearance frequency of this reference atomic arrangement in the reference compound.

The reference atomic arrangement is an atomic arrangement extracted from the reference compound. The atomic arrangement is extracted for each number of bonds. Since the extracted reference atomic arrangement is used in the step (Step S18) of calculating a partial score described later, in the same manner as in an atomic arrangement to be extracted from the compound to be evaluated, at least a reference atomic arrangement corresponding to the atomic arrangement is extracted. For example, the extraction is performed under the same conditions such as the number of bonds from an atom of interest, a structure of the atomic arrangement, and an electronic state of the atom. These conditions are not particularly limited as long as the conditions are the same as in the atomic arrangement extracted from the compound to be evaluated. For example, as the structure of the atomic arrangement, an atomic arrangement having a linear form, a branched form, a cyclic form, or a combination thereof can be extracted. In addition, in a case where electronic states of atoms are different from each other, it is preferable that the reference atomic arrangement and the atomic arrangement are extracted as different atomic arrangements. For example, in a carbon-carbon bond, an $SP^1$ hybrid orbital, an $SP^2$ hybrid orbital, and an $SP^1$ hybrid orbital are preferably extracted as different atomic arrangements. Furthermore, in a bond having a hydrogen atom in an end portion, in a case where a bond with the hydrogen atom does not need to be particularly considered, it is preferable that the extraction is performed such that the number of bonds does not include the bond with the hydrogen atom. Since the appearance frequency increases in a case of including the bond having a hydrogen atom in the end portion, the partial score and total score cannot be evaluated accurately.

Next, the reference appearance frequency of the extracted reference atomic arrangement in the reference compound is obtained. The reference appearance frequency is obtained with regard to all of the reference compounds in the compound database selected in the step S10, or with regard to the reference compound extracted from the compound database.

Figure 6:
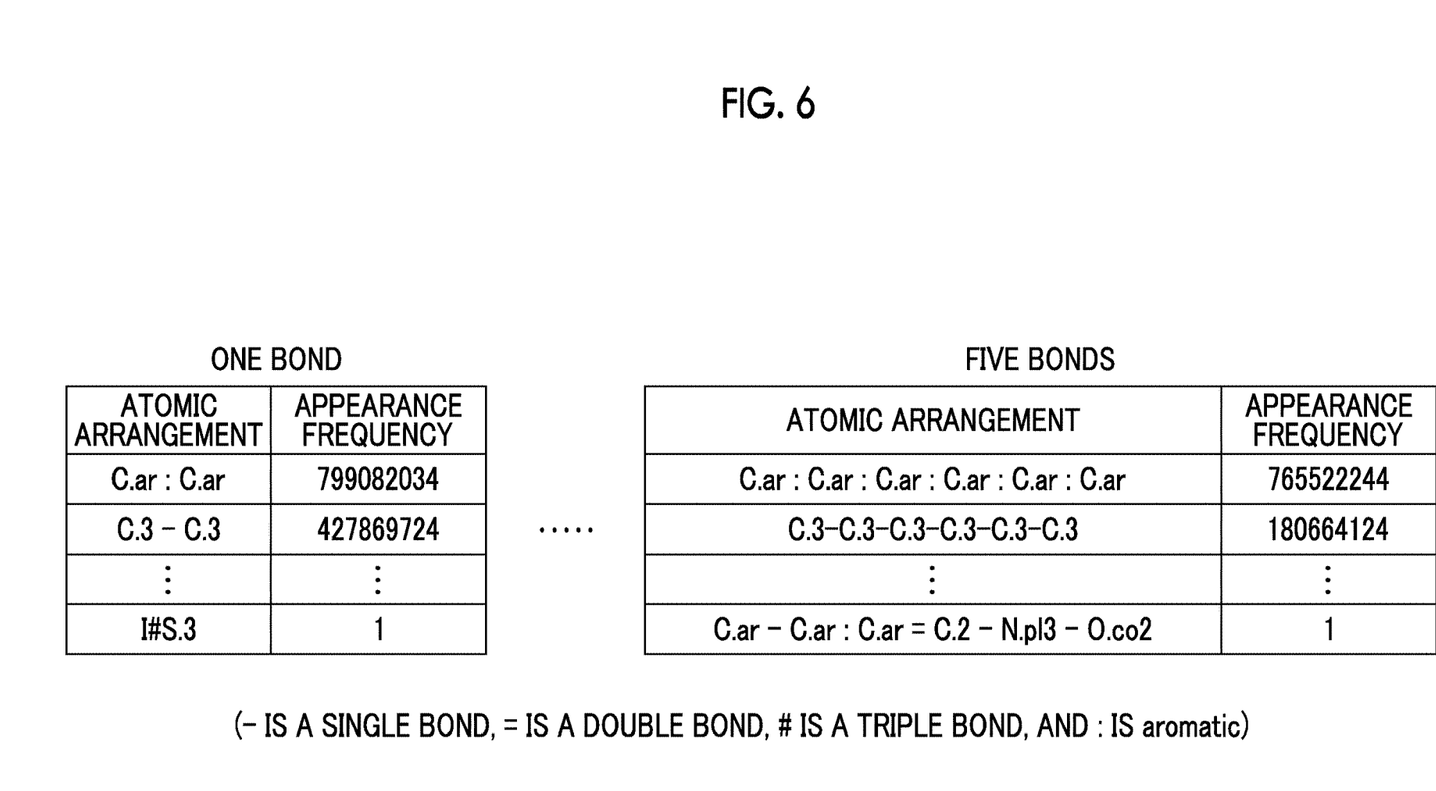
FIG. 6 is partial excerpts of tables showing extracted reference atomic arrangements and the number of reference appearance frequencies.

FIG. 6 is partial excerpts of tables showing extracted reference atomic arrangements and the number of appearance reference frequencies. In the present embodiment, atomic arrangements having a linear form, in which the number of bonds is up to 5, are extracted.

Atom names shown in the tables of FIG. 6 are atoms shown by Tripos Mol2 format. For example, a carbon of $sp^1$ hybrid orbital is represented by "C.1", a carbon of $sp^2$ hybrid orbital is represented by "C.2", a carbon of $sp^3$ hybrid orbital is represented by "C.3", and a carbon constituting an aromatic ring is represented by "C.ar". In addition, "-" between atoms means a single bond, "=" therebetween means a double bond, "#" therebetween means a triple bond, and ":" therebetween means aromatic. In addition, in the atom names shown in FIG. 6, "I" represents an iodine atom, "S.3" represents a sulfur atom of $sp^3$ hybrid orbital, "N.pl3" represents a nitrogen atom of a trigonal planar structure, and "O.co2" represents an oxygen atom in a carboxylic acid group and a phosphoric acid group. The tables shown in FIG. 6 show, as an example, a case of one bond (number of bonds is 1) and five bonds (number of bonds is 5), in which an atomic arrangement having the highest appearance frequency, an atomic arrangement having the second highest appearance frequency, and an atomic arrangement having the lowest appearance frequency is included, but in fact, there are many atomic arrangements, and the number of atomic arrangements in one bond is approximately 1 million. Since the reference atomic arrangement is extracted by the number of bonds from the atom of interest and the structure, in one benzene ring of the reference compound, the appearance frequency of "C.ar:C.ar" is "6", and the appearance frequency of "C.ar:C.ar:C.ar:C.ar:C.ar:C.ar" is "6".

<Step of Extracting Atomic Arrangement and Obtaining Appearance Frequency (Step S16)>

The step of extracting an atomic arrangement and obtaining an appearance frequency is a step of extracting an atomic arrangement from the structure of the compound input in the step S12, and obtaining an appearance frequency.

The extraction of the atomic arrangement can be performed in the same manner as the method of extracting the reference atomic arrangement in the step S16. In addition, with respect to the extracted atomic arrangement, the appearance frequency in the compound input in the step S12 is obtained.

Figure 7:
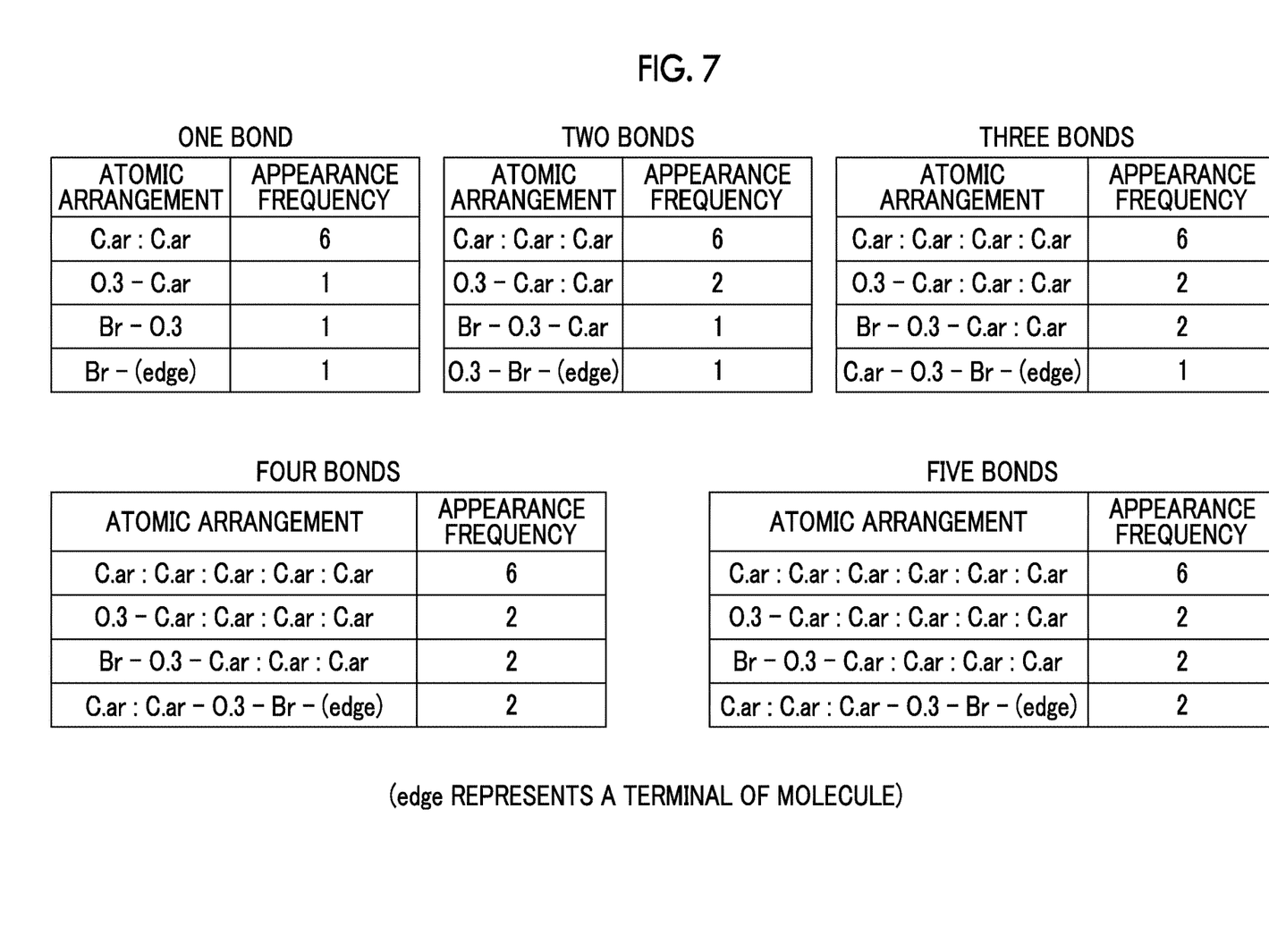
FIG. 7 is tables showing extracted atomic arrangements of the compound to be evaluated and frequencies of appearance.

FIG. 7 is tables showing, with respect to the compound input in the step S12, extracted atomic arrangements and frequencies of appearance of the atomic arrangements in the compound. Even in the step of extracting an atomic arrangement and obtaining an appearance frequency, same as in the step S14, atomic arrangements are extracted under the conditions that the number of bonds of atoms is 1 to 5, atomic arrangements have a structure of a linear form, and an atomic arrangement in which the terminal is a bond of a hydrogen atom is not included, and frequencies of appearance are obtained. "-(edge)" in the tables represents that the atom is the terminal of the structural formula.

<Step of Calculating Partial Score (Step S18)>

The step of calculating a partial score is a step of calculating, as a partial score, a frequency with which the atomic arrangement of the compound to be evaluated for the synthetic aptitude appears in the reference compound in the compound database.

As an expression (function) for calculating the partial score, a monotonically decreasing function or a monotonically increasing function can be used. As the function, for example, an inverse proportional function, an exponential function, and the like can be used. As the monotonically decreasing function, a function, in which the value decreases as the number (n) of bonds included in the atomic arrangement and/or the frequency (f) of appearance of the atomic arrangement in the reference compound in the compound database increase, can be used. In a case where the number of bonds included in the atomic arrangement increases, the reference appearance frequency in the reference compound decreases. However, in the atomic arrangement with a large number of bonds, there is an atomic arrangement which has a simple structure and is easy to synthesize, but in which the reference appearance frequency is low due to that the number of bonds is large. For example, in a case where the reference compound is propane ($CH_3CH_2CH_3$), the appearance frequency of an atomic arrangement of C.3-C.3 is "2", and the appearance frequency of C.3-C.3-C.3 is "1". As described above, even in a case of a compound which is easy to synthesize, a difference in synthetic aptitude occurs in a case where the score is calculated from the reference appearance frequency. In the present embodiment, since a function in which the number of bonds included in the atomic arrangement is also considered as a variable is used, the numerical value of the partial score decreases as the number of bonds increases. As a result, it is possible to reduce the influence of a large (the number of bonds is large) atomic arrangement (complex atomic arrangement which tends to be a unique arrangement of molecule) on an atomic arrangement in which the number of bonds is small and the reference appearance frequency is high. Therefore, comparing with a score simply obtained from the appearance frequency, the synthetic aptitude can be evaluated properly.

In addition, in a case where the frequency f of appearance is 0, that is, a case where an atomic arrangement extracted from the compound does not appear in the reference compound, it is preferable to use a function having no singular point. The atomic arrangement in which the frequency f of appearance is 0 is considered to be an atomic arrangement which is unlikely to exist as an atomic arrangement of a compound in the related art. Therefore, a compound with such an atomic arrangement should be evaluated as a compound having low synthetic aptitude, but since the score cannot be calculated in a case where a singular point is present at f=0, the contribution from such an atomic arrangement is ignored in the evaluation of synthetic aptitude. As a result, the score may indicate that the compound has the synthetic aptitude, which is a case where the synthetic aptitude is not evaluated properly. By using a function having no singular point at the frequency f of appearance is 0, the synthetic aptitude can be evaluated properly.

As a function used for the calculation of the partial score, for example, functions shown by Expression (1) and Expression (2) can be used.

$$s(substr) = \left[\frac{1}{n(substr) \times (f(substr) + 1)}\right]^d \quad \text{Expression (1)}$$

$$s(substr) = \exp\left[-\left(\frac{n(substr) - 1}{\sigma_n}\right)^{d_n}\right] \exp\left[-\left(\frac{f(substr)}{\sigma_f}\right)^{d_f}\right] \quad \text{Expression (2)}$$

In the expressions, substr is an atomic arrangement included in the compound to be evaluated, and s is a partial score. n is the number of bonds included in the atomic arrangement, and f is a reference appearance frequency in the compound database. d, $d_n$, and $d_f$ are parameters, and by changing the numerical values of d, $d_n$, and $d_f$, the numerical value of s(substr) can be changed. The partial score can be increased by increasing the value of d, and the partial score can be decreased by increasing the values of $d_n$ and $d_f$. In addition, $\sigma_n$ and $\sigma_f$ are parameters, and by changing the numerical values of $\sigma_n$ and $\sigma_f$, the numerical value of s(substr) can be changed. The partial score can be increased by increasing the values of $\sigma_n$ and $\sigma_f$. Expression (1) and Expression (2) are monotonically decreasing functions, and in a case where a monotonically increasing function is used, the interpretation of the obtained score is reversed, that is, it can be determined that the synthetic aptitude is higher as the obtained score is higher.

Next, an example of calculating the partial score will be described. As an example, a partial score of C.ar:C.ar (carbon-carbon bond in an aromatic ring) which is an atomic arrangement of one bond will be calculated. As an expression for obtaining the partial score, Expression (1) described above is used. In addition, the parameter d is set to "1".

First, a partial score of the atomic arrangement C.ar:C.ar in the reference compound of the compound database (PubChem) is calculated. Since the appearance frequency of the atomic arrangement C.ar:C.ar in the reference compound of the compound database (PubChem) is 799082034, s(C.ar:C.ar) is $1/(1\times(799082034 \div 1)) = 1.25 \times 10^{-9}$.

Next, based on the partial score of the atomic arrangement C.ar:C.ar in the reference compound of the compound database (PubChem), a partial score of C.ar:C.ar in the compound for which the synthetic aptitude is evaluated is calculated. Since the appearance frequency of C.ar:C.ar in the compound for which the synthetic aptitude is evaluated is "6", the partial score of C.ar:C.ar in the compound for which the synthetic aptitude is evaluated is $1.25 \times 10^{-9} \times 6 = 7.5 \times 10^{-9}$.

In addition, since the appearance frequency of the atomic arrangement Br—O.3—C.ar:C.ar:C.ar:C.ar in the reference compound of the compound database is 670, s(Br—O.3—C.ar:C.ar:C.ar:C.ar) is $1/(5\times(670\div1))=2.98\times10^{-4}$. Since the appearance frequency of Br—O.3—C.ar:C.ar:C.ar:C.ar in the compound to be evaluated for the synthetic aptitude is "2", the partial score is $2.98\times10^{-4}\times2=5.96\times10^{-4}$.

As described above, the partial score can be decided by a balance between the number of bonds in the atomic arrangement and the appearance frequency in the reference compound of the compound database.

In the step S18, partial scores are calculated for all of the atomic arrangements shown in the tables of FIG. 7. In FIG. 7, the number of bonds is 5 and the atomic arrangement is linear, but depending on the type of an atomic arrangement to be extracted, partial scores of the atomic arrangement are also calculated.

<Step of Evaluating Synthetic Aptitude (Step S20)>

The step of evaluating the synthetic aptitude is a step of evaluating the synthetic aptitude from a total score obtained by totaling the partial scores.

The partial scores of the respective atomic arrangements calculated in the step S18 are totaled to obtain the total score. The total score can be obtained by totaling the partial scores. In a case where, with regard to the compound shown in FIG. 5, the partial scores of the respective atomic arrangements shown in FIG. 7 are calculated and a total score thereof is calculated, the total score is $7.17\times10^{-3}$.

Figure 8:
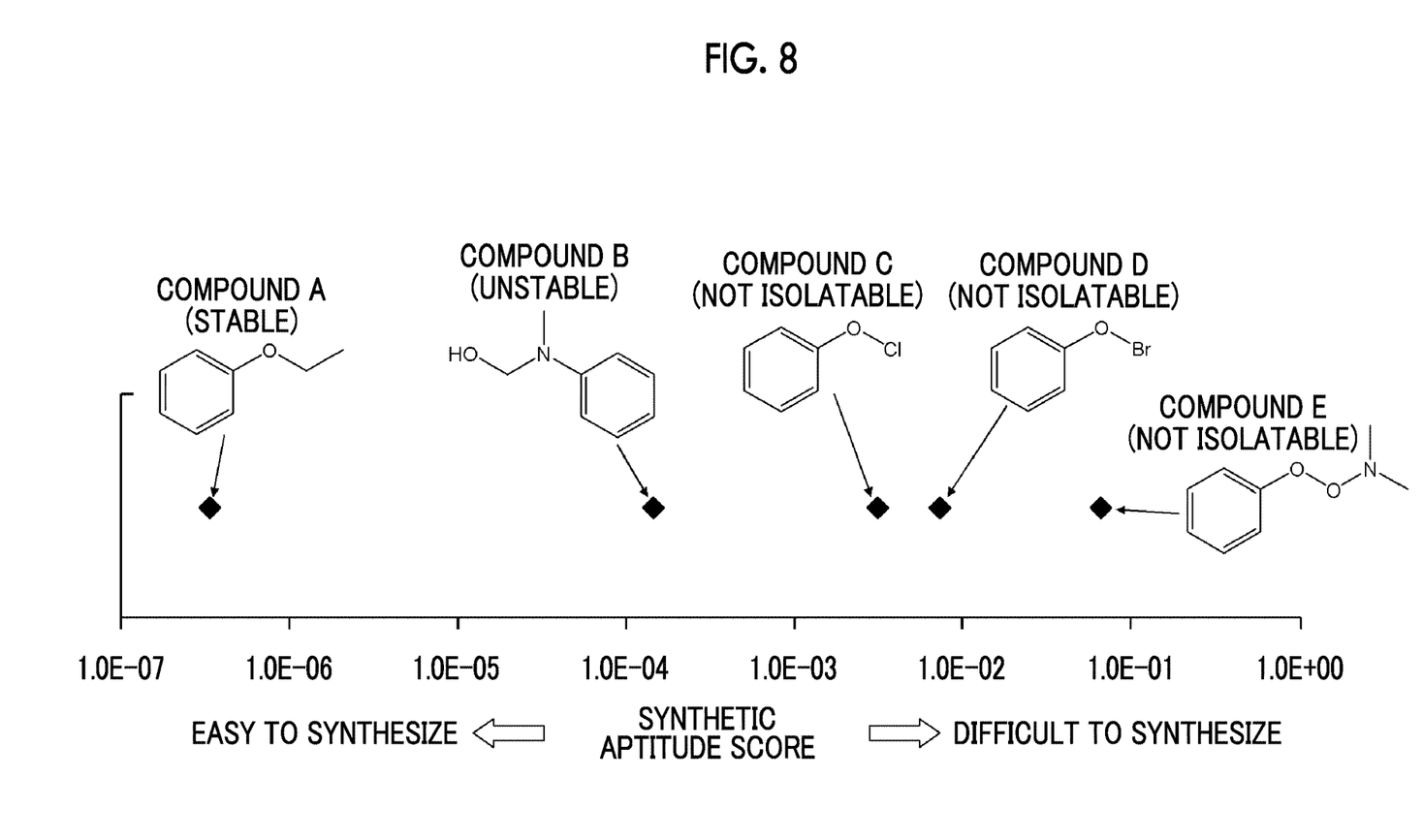
FIG. 8 is a diagram showing a relationship between a compound and a synthetic aptitude score.

FIG. 8 is a diagram in which compounds and synthetic aptitude scores are shown on the horizontal axis. The total score obtained in the step S18 is the synthetic aptitude score in the present embodiment. It can be evaluated that the synthesis is easier as the synthetic aptitude score is smaller, and it can be determined that the synthesis is more difficult as the synthetic aptitude score is larger. Among compounds A to E shown in FIG. 8, the compound D is a compound, as an example of the present embodiment, for which the total score is obtained. The compound A is known for a synthesizable compound, that is, a compound which is stable under the atmosphere at ordinary temperature and pressure and is isolatable. The compound B is known for a compound which is isolatable, but which is unstable under the atmosphere at ordinary temperature and pressure and has no synthetic aptitude. The compounds C to E are known for a compound which also has no synthetic aptitude because the isolation is not possible under the atmosphere at ordinary temperature and pressure. As shown in FIG. 8, it can be confirmed that a compound having lower total score (synthetic aptitude score) is more synthesizable and stable. Therefore, by calculating the total score (synthetic aptitude score), the synthetic aptitude of the compound can be evaluated without actually performing the synthesis. It should be noted that, as a parameter is used in a case of calculating the partial score, the total score (synthetic aptitude score) does not perform the evaluation of the synthetic aptitude (easy or difficult to synthesize) at a certain score or higher, but performs the evaluation by comparison with other compounds.

In the present embodiment, the partial score is calculated for each of the atomic arrangements to be quantified, and the synthetic aptitude is evaluated by the total score totaling the partial scores. However, the present embodiment is not limited thereto. Instead of quantifying, a partial evaluation may be performed for each of the atomic arrangements, and a total evaluation is performed by totaling the partial evaluations.

Figure 9:
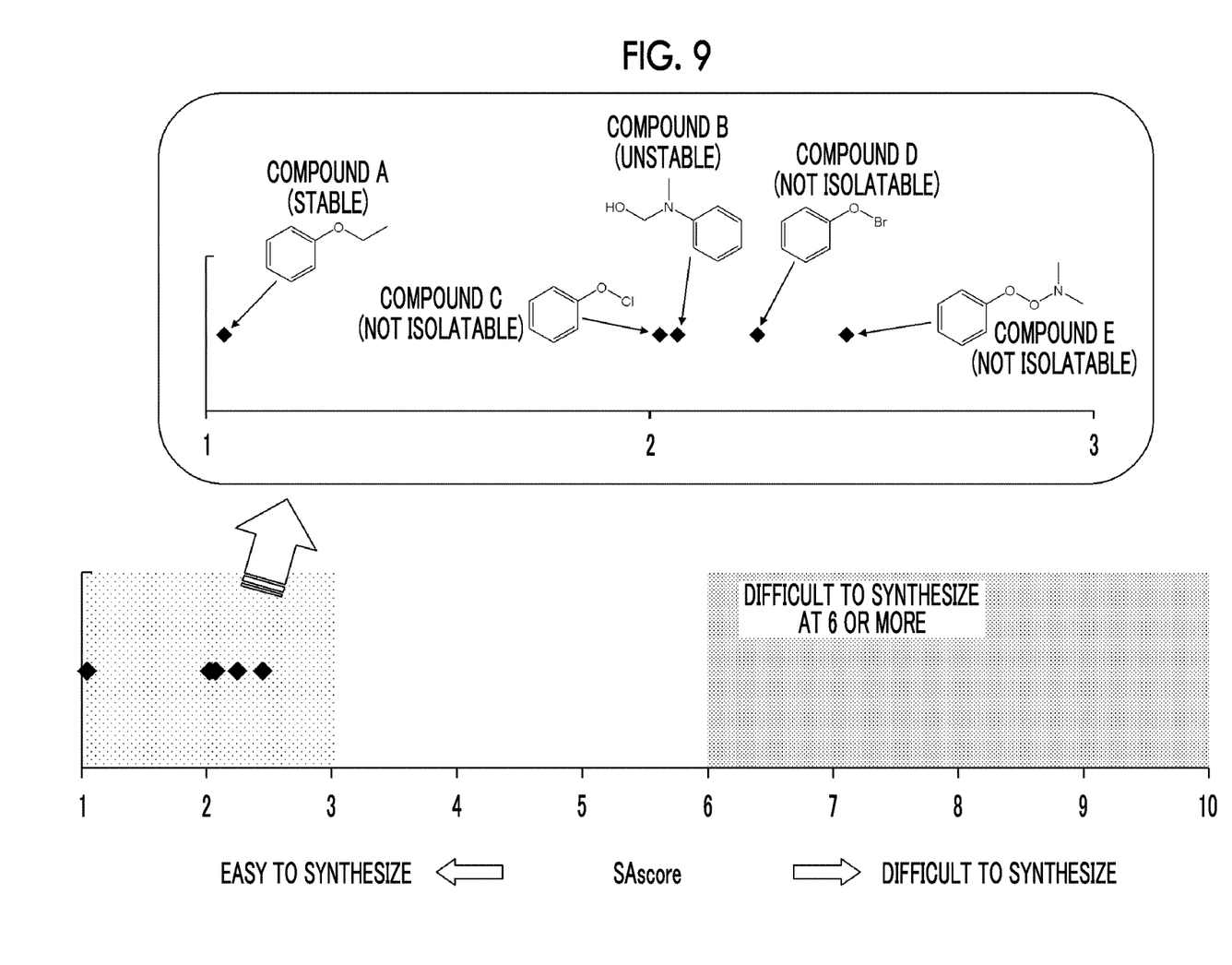
FIG. 9 is a diagram showing a relationship between a compound and SAscore.

FIG. 9 is a diagram showing a relationship between SAscore and a compound. It is evaluated that the synthesis is difficult in a case where SAscore is 6 or more. As shown in FIG. 9, since the compound B which is unstable and the compounds C to E which are non-synthesizable compounds are in a range in which SAscore is 2 to 3, it is determined that the compounds have the synthetic aptitude.

Figure 10:
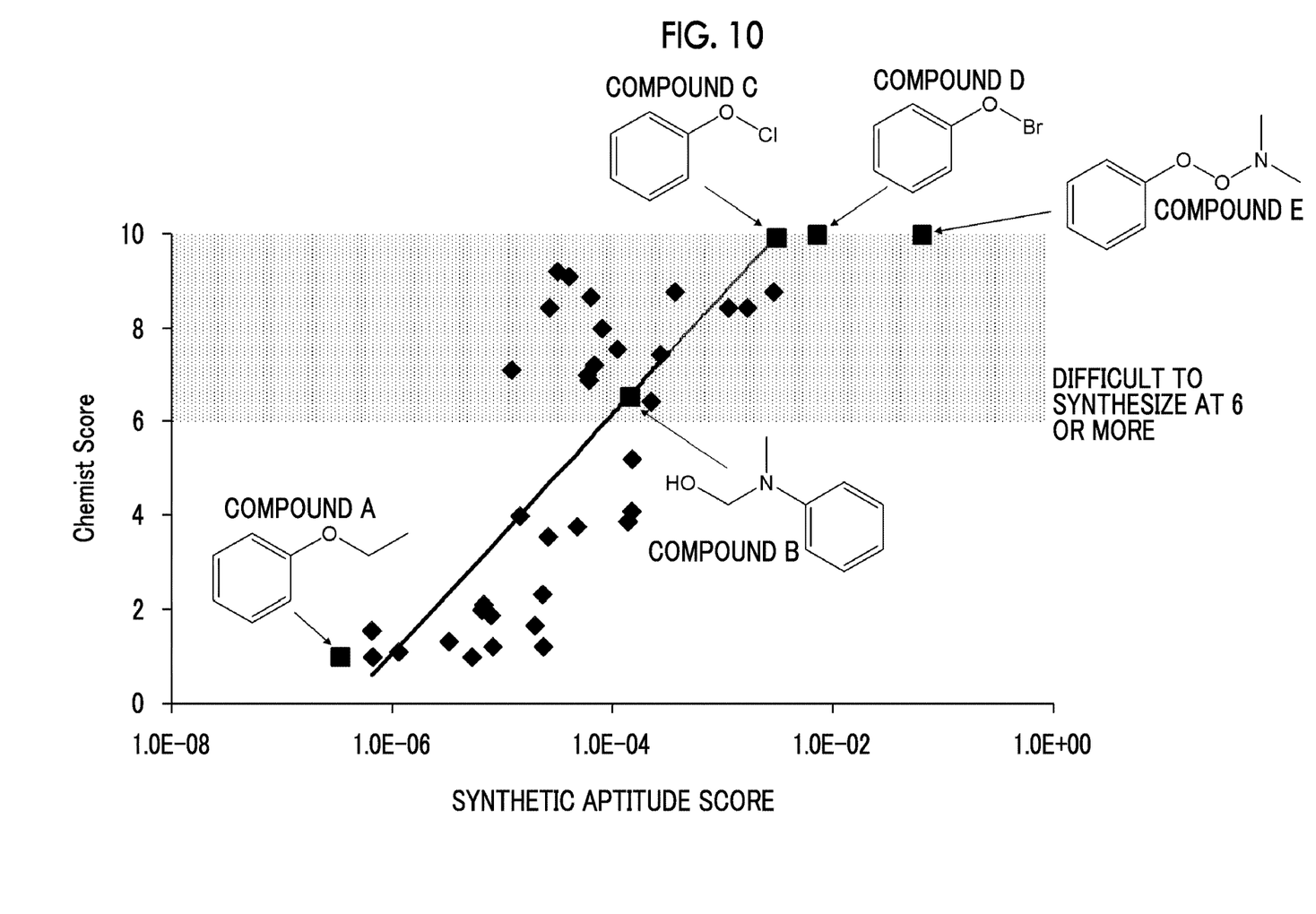
FIG. 10 is a diagram showing a relationship between ChemistScore and a synthetic aptitude score.

In addition, FIG. 10 is a diagram showing a relationship between ChemistScore and the total score obtained in the present embodiment. ChemistScore is a score disclosed in "Estimation of synthetic Accessibility score of drug-like molecules based on molecular complexity and fragment contributions", Peter Ertl and Ansgar Schuffenhauer, Journal of Cheminformatics 2009, 1;8, "searched on Jul. 23, 2018", internet (jcheminf.springeropen.com/articles/10.1186/1758-2946-1-8), and is a score which is ranked by chemists with regard to the ease of synthesizing a compound. It can be determined that a compound having ChemistScore of 6 or more is difficult to synthesize. As shown in FIG. 10, comparing the total score (synthetic aptitude score) obtained in the present embodiment with ChemistScore, in a score equal to or more than the score determined to be difficult to synthesize by ChemistScore, the total score of the present embodiment also determines to be difficult to synthesize. Therefore, it is considered that, as evaluation criteria for the synthetic aptitude, the total score can evaluate the aptitude.

<Effects of Method for Evaluating Synthetic Aptitude of Compound and Program for Evaluating Synthetic Aptitude of Compound>

As described above, using the method for evaluating a synthetic aptitude of a compound and program for evaluating a synthetic aptitude of a compound according to the present embodiment, the device 10 for evaluating a synthetic aptitude of a compound can properly evaluate the synthetic aptitude of the compound, particularly the synthetic aptitude of a compound generated or modified on a computer.

Explanation of References

10: device for evaluating synthetic aptitude of compound
100: processing part
105: database selection part
110: structure acquisition part
115: first extraction part
120: second extraction part
125: calculation part
130: evaluation part
135: output part
140: display control part
145: CPU
150: ROM
155: RAM
200: storage part
205: structure information
210: reference compound information
215: atomic arrangement information
220: appearance frequency information
225: reference atomic arrangement information
230: reference appearance frequency information
235: function information
300: display part
310: monitor
400: operation part
410: keyboard
420: mouse
500: external server
510: external database
NW: network

What is claimed is:

1. A computer-implemented method for evaluating a synthetic aptitude of a compound, the method comprising:
   receiving, via an input device, from a user, input identifying a structure of a compound for which the synthetic aptitude is evaluated, a compound database, and specification of an atomic arrangement to be extracted;
   selecting, based on the input that was received from the user, the compound database storing a plurality of reference compounds which serve as evaluation criteria for a synthetic aptitude;
   deciding, based on the input that was received from the user, the structure of the compound to be evaluated for the synthetic aptitude;
   extracting a reference atomic arrangement from a structure of the reference compound stored in the compound database and obtaining a reference appearance frequency of the reference atomic arrangement;
   extracting, based on the input that was received from the user, the atomic arrangement from the structure of the compound and obtaining an appearance frequency of the atomic arrangement;
   evaluating the synthetic aptitude based on the number of bonds included in the atomic arrangement of the compound and the appearance frequency of the reference atomic arrangement corresponding to the atomic arrangement, and
   displaying, on a display, a result of the evaluating the synthetic aptitude, the display including a plurality of regions indicating a range where synthesis is non-synthesizable to where there is synthetic aptitude,
   wherein, in the evaluating the synthetic aptitude, a partial score is calculated for each of the atomic arrangements to be quantified, and the evaluation is performed by a total score totaling the partial scores, and
   wherein the calculation of the partial score uses a function having no singular point in a case where the appearance frequency of the atomic arrangement in the compound database is 0.

2. The method for evaluating a synthetic aptitude of a compound according to claim 1,
   wherein, in the evaluating the synthetic aptitude, a partial evaluation is performed for each of the atomic arrangements, and a total evaluation is performed by totaling the partial evaluations.

3. The method for evaluating a synthetic aptitude of a compound according to claim 1, the method further comprising:
   evaluating, from the total score, a similarity between the compound and a feature of the reference compound stored in the compound database.

4. The method for evaluating a synthetic aptitude of a compound according to claim 1
   wherein, in the evaluating the synthetic aptitude, the evaluation is performed using a monotonically decreasing function or a monotonically increasing function.

5. The method for evaluating a synthetic aptitude of a compound according to claim 1,
   wherein the reference atomic arrangement and atomic arrangement extracted are a linear form, a branched form, a cyclic form, or a combination thereof.

6. The method for evaluating a synthetic aptitude of a compound according to claim 1,
   wherein the reference atomic arrangement and the atomic arrangement are extracted as different atomic arrangements in a case where electronic states in atoms therebetween are different from each other.

7. The method for evaluating a synthetic aptitude of a compound according to claim 1,
   wherein, in a case of extracting the atomic arrangement from the structure of the compound, an atomic arrangement in which an end portion of a bond is a hydrogen atom is not extracted.

8. A non-transitory and computer-readable recording medium having thereon computer instructions which causes, when read by a computer, the computer to execute a method for evaluating a synthetic aptitude of a compound, comprising:
   receiving, via an input device, from a user, input identifying a structure of a compound for which the synthetic aptitude is evaluated, a compound database, and specification of an atomic arrangement to be extracted;
   selecting, based on the input that was received from the user, the compound database storing a plurality of reference compounds which serve as evaluation criteria for a synthetic aptitude;
   deciding, based on the input that was received from the user, the structure of the compound to be evaluated for the synthetic aptitude;
   extracting a reference atomic arrangement from a structure of the reference compound stored in the compound database and obtaining a reference appearance frequency of the reference atomic arrangement;
   extracting, based on the input that was received from the user, the atomic arrangement from the structure of the compound and obtaining an appearance frequency of the atomic arrangement;
   evaluating the synthetic aptitude based on the number of bonds included in the atomic arrangement of the compound and the appearance frequency of the reference atomic arrangement corresponding to the atomic arrangement, and
   displaying, on a display, a result of the evaluating the synthetic aptitude, the display including a plurality of regions indicating a range where synthesis is non-synthesizable to where there is synthetic aptitude,
   wherein, in the evaluating the synthetic aptitude, a partial score is calculated for each of the atomic arrangements to be quantified, and the evaluation is performed by a total score totaling the partial scores, and
   wherein the calculation of the partial score uses a function having no singular point in a case where the appearance frequency of the atomic arrangement in the compound database is 0.

9. A device for evaluating a synthetic aptitude of a compound, the device comprising
   at least one processor configured to:
      receive, via an input device, from a user, input identifying a structure of a compound for which the synthetic aptitude is evaluated, a compound database, and specification of an atomic arrangement to be extracted;
      select, based on the input that was received from the user, the compound database storing a plurality of reference compounds which serve as evaluation criteria for a synthetic aptitude;
      acquire, based on the input that was received from the user, the structure of the compound to be evaluated for a synthetic aptitude;
      extract a reference atomic arrangement from a structure of the reference compound stored in the compound database, and obtain a reference appearance frequency of the reference atomic arrangement;
      extract, based on the input that was received from the user, the atomic arrangement from the structure of the compound and obtain an appearance frequency of the atomic arrangement;
      calculate, as a partial score, a frequency with which the atomic arrangement appears in the reference compound, and calculate a total score by totaling the partial scores, based on the number of bonds included in the atomic arrangement of the compound and the appearance frequency of the reference atomic arrangement corresponding to the atomic arrangement, using a function in which a numerical value decreases as the number of bonds included in the atomic arrangement and the appearance frequency increase;
      evaluate the synthetic aptitude based on the total score, and
      display, on a display, a result of the evaluating the synthetic aptitude, the display including a plurality of regions indicating a range where synthesis is non-synthesizable to where there is synthetic aptitude,
   wherein, in the evaluating the synthetic aptitude, a partial score is calculated for each of the atomic arrangements to be quantified, and the evaluation is performed by a total score totaling the partial scores, and
   wherein the calculation of the partial score uses a function having no singular point in a case where the appearance frequency of the atomic arrangement in the compound database is 0.

* * * * *